United States Patent
Schaak et al.

(10) Patent No.: US 9,469,838 B2
(45) Date of Patent: Oct. 18, 2016

(54) BIOFILM TREATMENT OF COMPOSITE MATERIALS CONTAINING MYCELIUM

(71) Applicants: Damen Donald Schaak, Troy, NY (US); Matthew James Lucht, Troy, NY (US)

(72) Inventors: Damen Donald Schaak, Troy, NY (US); Matthew James Lucht, Troy, NY (US)

(73) Assignee: Ecovative Design, LLC, Green Island, NY (US)

( * ) Notice: Subject to any disclaimer, the term of this patent is extended or adjusted under 35 U.S.C. 154(b) by 0 days.

(21) Appl. No.: 14/745,042

(22) Filed: Jun. 19, 2015

(65) Prior Publication Data
US 2015/0376565 A1 Dec. 31, 2015

Related U.S. Application Data

(60) Provisional application No. 62/017,315, filed on Jun. 26, 2014.

(51) Int. Cl.
  *C12N 1/14* (2006.01)
  *C12N 1/20* (2006.01)
(52) U.S. Cl.
  CPC .. *C12N 1/20* (2013.01); *C12N 1/14* (2013.01)
(58) Field of Classification Search
  CPC .................................. C12N 1/20; C12N 1/14
  See application file for complete search history.

(56) References Cited

U.S. PATENT DOCUMENTS

| | | | |
|---|---|---|---|
| 2004/0166576 A1* | 8/2004 | Sadaie | C02F 3/34 435/262.5 |
| 2008/0234210 A1* | 9/2008 | Rijn | A01N 43/90 514/28 |

OTHER PUBLICATIONS

Wang et al. "Influence of fungal elicitors on biosynthesis of natamycin by Streptomyces natalensis HW-2" Appl Microbiol Biotechnol (2013) 97:5527-5534.*
Yang et al. "Medicinal Mushroom Ganoderma lucidum as a Potent Elicitor in Production of t-Resveratrol and t-Piceatannol in Peanut Calluses" J. Agric. Food Chem. 2010, 58, 9518-9522.*
Perez et al. "Myxococcus xanthus induces actinorhodin overproduction and aerial mycelium formation by Streptomyces coelicolor" Microb Biotechnol. Mar. 2011; 4(2): 175-183.*

* cited by examiner

*Primary Examiner* — Louise W Humphrey
*Assistant Examiner* — Stephen A Perkins
(74) *Attorney, Agent, or Firm* — Francis C. Hand; Carella, Byrne et al.

(57) ABSTRACT

The process provides a biofilm including and not limited to cellulose produced by bacteria that can be used as a bio-resin and as a surface application for myceliated and non-myceliated biomaterials.

In one embodiment, the process comprises the steps of obtaining an agricultural substrate; and cohabitating a selected bacteria with a selected fungus in the agricultural substrate for a period of time to allow the bacteria to grow alongside the fungus and to excrete a biofilm from the bacteria into the substrate to provide bio-resin like strengthening compounds to the agricultural substrate.

5 Claims, 3 Drawing Sheets

BIOFILM TREATMENT OF COMPOSITE MATERIALS CONTAINING MYCELIUM

This invention claims priority of Provisional Patent Application 62/017,315 filed Jun. 26, 2014.

This invention relates to a process that provides a biofilm including and not limited to cellulose produced by bacteria that can be used as a bio-resin and as a surface application for myceliated and non-myceliated biomaterials. More particularly, this invention relates to a biofilm treatment of myceliated biomaterials.

BACKGROUND OF THE INVENTION

Biofilms are comprised of excreted protein, DNA, and polysaccharides that tend to form a complex matrix consisting of organic and nonorganic materials. These biofilms contain the cells that produced them providing the cells with a film or slim to live on. [Karatan, E., Watnick, P. (June 2009). "Signals, Regulatory Networks, and Materials That Build and Break Bacterial Biofilms"].

The production of biofilms can provide bacterium an anchor or platform to grow from and serve as a protective barrier from the environment. Polysaccharides typically encapsulate the biofilms providing a bound matrix of living and nonliving organic matter. [Hall-Stoodley L, Costerton J W, Stoodley P (February 2004). "Bacterial biofilms: from the natural environment to infectious diseases"]

Biofilms can provide the bacteria a sanctuary from antibiotics, desiccation, and nutritional stress. Some biofilms produced from bacteria are composed of single polysaccharides like microbial cellulose.

As is known, U.S. patent application Ser. No. 12/001,556, filed Dec. 12, 2007, describes various techniques for making a biomaterial composed of a substrate of discrete particles and a network of interconnected mycelia cells extending through and around the discrete particles and bonding discrete particles together.

It is an object of the invention to provide improvements to the methods of making biomaterials.

It is another object of the invention to provide improvements to the methods of making myceliated biomaterials and non-myceliated biomaterials.

It is another object of the invention to utilize bacterial biofilms to provide biomaterial materials such as described in U.S. patent application Ser. No. 12/001,556 with an added resin matrix and surface layer.

Briefly, the invention provides a process by which biofilms including and not limited to cellulose produced by bacteria can be used as a bio-resin and as a surface application for myceliated and non-myceliated biomaterials.

In particular, the process comprises the steps of obtaining an agricultural substrate; and cohabitating a selected bacteria with a selected fungus in the agricultural substrate for a period of time to allow the bacteria to grow alongside the fungus and to excrete a biofilm from the bacteria into the substrate to provide bio-resin like strengthening compounds to the agricultural substrate.

In accordance with the techniques described in U.S. patent application Ser. No. 12/001,556, the fungus grows a network of interconnected mycelia cells extending through and around discrete particles of the substrate to bond the discrete particles together into a self-supporting composite material.

In one embodiment, the bacteria will be cohabitated with a selected fungus in agricultural substrates (AS), e.g. corn stalks. During this cohabitation period, the bacteria will grow alongside the fungal strains and excrete biofilms into the substrate providing bio-resin like strengthening compounds to the self-supporting composite material.

In another embodiment, the bacteria may be grown in vitro, thus producing a biofilm, which would then be harvested and applied to the AS at various stages of the growth process and in some instances encapsulating the material in a biofilm like skin. These in vitro applications would be applied to both the internal and external surfaces of the biomaterials. Some bacterial strains will be genetically engineered to optimize biofilm quality, excretion levels, and induction. In this embodiment, the biofilm may be applied to myceliated substrates, i.e. a substrate wherein the fungus grows a network of interconnected mycelia cells extending through and around discrete particles of the substrate, or the biofilm may be applied to non-myceliated substrates.

Utilizing genetic engineering techniques, inducible controlling sequences may be inserted into the bacterial genome to regulate biofilm production and various other biofilm components. Inducible gene expression will be regulated by photoreceptors, temperature signaling, small molecules, constitutively expressed promoters, or through knocking out genes.

Agricultural substrates are vulnerable to unwanted microbial bio burden that can cause the growing material to become contaminated. These contaminated materials fail to grow properly thus reducing product yields and performance. Here, the antimicrobial properties of some bacteria species are to be harnessed. Both bacteria and fungi species will be cohabitated together in the selected agricultural substrates (e.g. corn stalks). In this particular application, the bacteria will excrete antimicrobial compounds that reduce the competition between unwanted microbes and the selected fungal species. This strategy will enhance the ability of the fungus to resist external bio burden commonly growing throughout the selected agricultural substrates. Molecular genetic techniques are also utilized to reprogram the bacteria strains to overexpress antimicrobials both in vitro, and in situ.

These and other objects of the invention will become more apparent from the following detailed description taken in conjunction with the accompanying drawings wherein.

Figure 1:
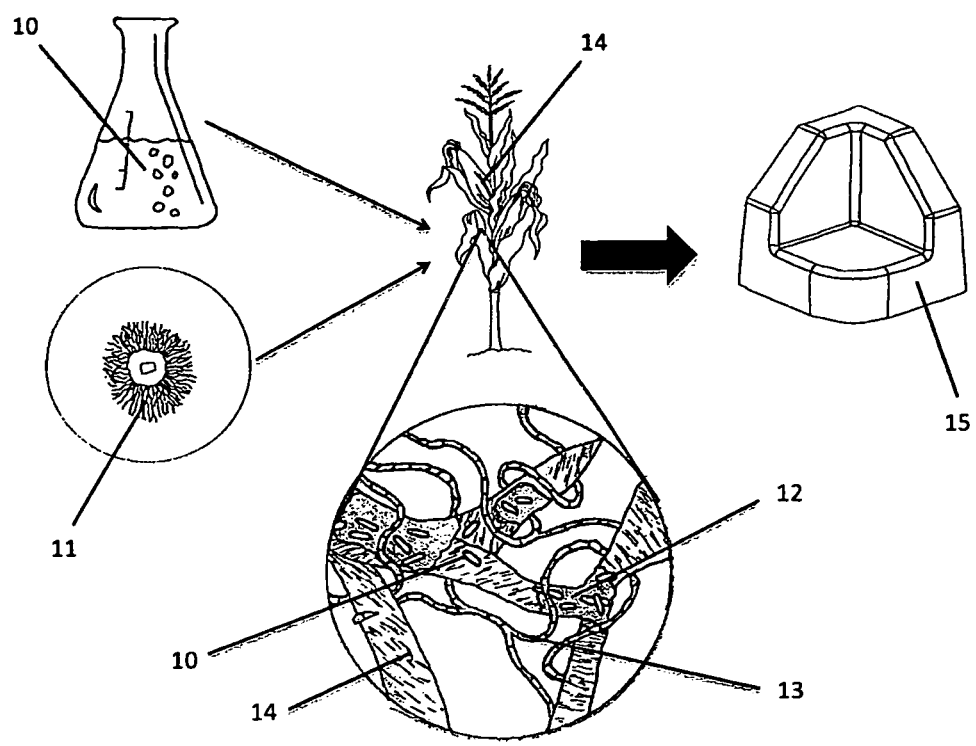
FIG. 1 illustrates a schematic of the steps of a process in accordance with the invention.

Referring to FIG. 1, in accordance with one embodiment of the process of the invention, a liquid medium of a bacteria culture (a *Bacillus subtilis* species) is first prepared, for example, in a flask 10, along with the preparation of fungal mycelium, for example, on an agar plate 11.

Thereafter the bacteria culture and fungal mycelium are applied to an agricultural substrate, for example, corn stalks.

As illustrated, during incubation of the agricultural substrate, the bacteria produces a biofilm (bioresin) 12 while the fungal mycelium grows hyphae 13 that grow to form a network of interconnected mycelia cells extending through and around discrete particles 14 of the agricultural substrate to bond the discrete particles together into a self-supporting composite material, i.e. the finished product 15.

As indicted, the finished product 15 is a biomaterial, i.e. a molded block, that can be used for protective packaging.

FIG. 1 represents the ability of a fungus and bacteria strains to cohabitate.

Figure 2:
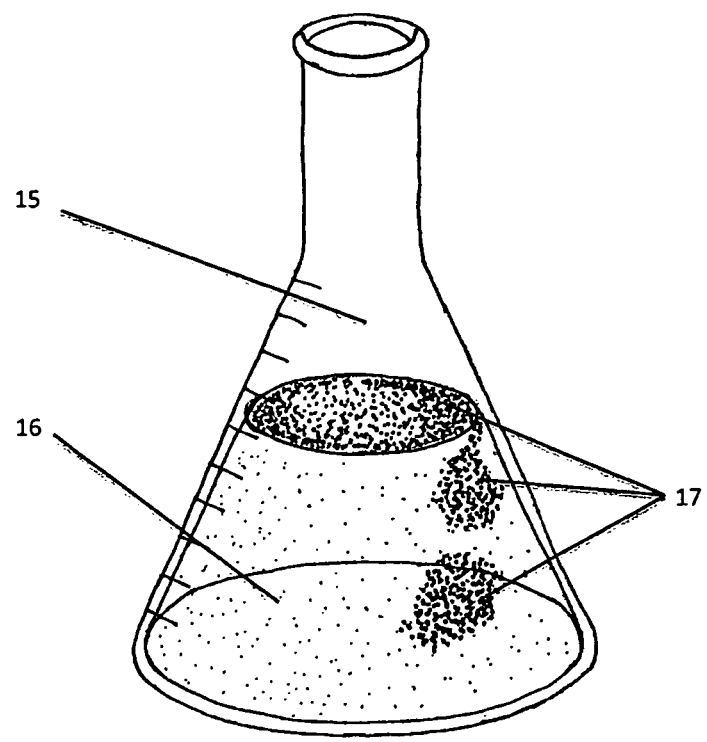
FIG. 2 illustrates photoimages of a flask containing a biofilm produced in vitro in accordance with the invention.

Process Steps for Growing Biofilms Grown In Situ:
a. Inoculate the media that has specificity to the bacteria being cultured with one colony of bacteria. Grow the bacterial culture until the culture reaches mid log phase.
  In this step, the bacteria strain was inoculated into lysogeny broth (LB) and grown to optimal cell density. The quantities of the LB medium are dependent on the bacterial strain used and the quantity of agricultural substrate the LB is inoculated into. For *Bacillus subtilis* (bacteria strain), the agricultural substrate was inoculated at 1:6 (1 milliliter of bacterial culture: 6 grams dry agricultural substrate).
b. Add bacterial culture grown to mid log phase to either myceliated or non-myceliated agricultural substrate (AS). If preparing "myceliated AS", co-inoculate the AS with the bacteria culture and one of the selected fungal species. If "non-myceliated AS" is prepared, the AS will only be inoculated with the bacterial culture. The biofilm produced by the bacteria will be the sole microbial bioresin in the substrate.
  In this step, the agricultural substrate was simultaneously inoculated with both *Ganoderma* (fungus) and a *Bacillus subtilis* species (bacteria)
c. Incubate the biomaterial until the AS is fully colonized with the added bacteria and/or fungal mycelium.
  In this step, the biomaterial was incubated for 6 days
d. Terminate growth of materials by method of desiccation.
  In this step, the biomaterial was dried to terminate microbial growth.
  Referring to FIG. 2, wherein like reference characters indicate like parts as above, a process for producing a bacterial biofilm in vitro employs a flask 15, into which a biofilm excreting bacteria 16 is placed.

Process Steps for Growing Biofilms Grown In Vitro:
a. Inoculate medium with bacteria (as above)
b. Incubate culture at optimal conditions for the desired time
c. Harvest the biofilm (17)
d. Apply the biofilm to the myceliated or non-myceliated substrate
e. Either continue to grow out materials or terminate growth.

Applications
I. Bacterial Biofilms Produced In Situ.
  a. As a means of binding together discrete lignocellulose particles (both as a sole microbial component and in combination with other bacteria and fungi). Growing the biofilm-producing bacteria directly into the myceliated and non-myceliated biomaterial (in situ) to provide the cohabitated substrate with the addition of a biofilm that will act as both a resin for strength and particle bonding.
  b. As a surface application for altering physical properties and aesthetics. Once the material has finished growing, the biofilm will have been excreted throughout the material (internal and external surfaces). The extent to which the biofilm coats the external surfaces of the finished material is dependent on the bacteria species used during cohabitation and the resultant biofilm produced.
  c. As a nutrition source for cohabitating fungi. The organic material accumulated throughout the production of the biofilm may also become a source of nutrition for other bacteria and fungal species growing in the substrate.

II. Bacterial Biofilms Produced In Vitro.
  a. As a means of binding together discrete lignocellulose particles (both as a sole microbial component, and in combination with other bacteria and fungi).
  b. As a surface application for altering physical properties and aesthetics.
  c. As a nutrition source for cohabitating fungi. The organic material accumulated throughout the production of the biofilm may also become a source of nutrition for other bacteria and fungal species growing in the substrate.

III. Genetically Engineered Biofilm Producing Bacteria Strains
  a. Genetically modified biofilm dependent genes will allow for optimal levels of biofilm production. This will be done through bacterial controlling sequences specifically engineered for our species of bacteria and their associated biofilms.
  b. Provide the capability to induce biofilm production at selected time points during material growth. This will be done through bacterial controlling sequences, which will be regulated through photoreceptors, temperature signaling, small molecules or constitutive promoters.

IV. Bacterial Antimicrobials Produced In Situ
  a. As a means to cohabitate both fungi and bacteria species together with the purpose of reducing the background bio burden residing in our agricultural substrates throughout the materials growth process.

V. Bacterial Antimicrobials Produced In Vitro
  a. Culture antimicrobial producing bacteria in vitro (liquid media). Use the antimicrobial spiked culture as a bio burden treatment to agricultural substrates.

VI. Genetically Engineered Antimicrobial Producing Bacteria
  a. Through genetic modifications, reprogram the cohabitating bacteria to express or overexpress antimicrobials in both in vitro and in situ paradigms.

The following are specific examples of the process for making a biofilm.

EXAMPLE 1

Grow Biofilm-Producing Bacteria into Myceliated Substrate a. Inoculate 25 ml Lysogeny Broth (LB) with one colony of *Bacillus subtilis* sp. (bacteria), grow overnight at 37° C.
a. Passage the culture (1:10) into 250 ml LB media, and continue incubation until the culture reaches mid log phase.
b. Co-inoculate the AS with both fungal and bacterial species using <20% fungal v/v inoculum, and 1 ml of log phase bacteria culture per 6 grams of dry AS.
c. Incubate the co-inoculated AS for 2-10 days.
d. Hot press the material (10 minutes at 400° F., held under 350 psi of platen pressure.) to bond all components if applicable to material performance.
e. Terminate growth of material

EXAMPLE 2

Figure 3:
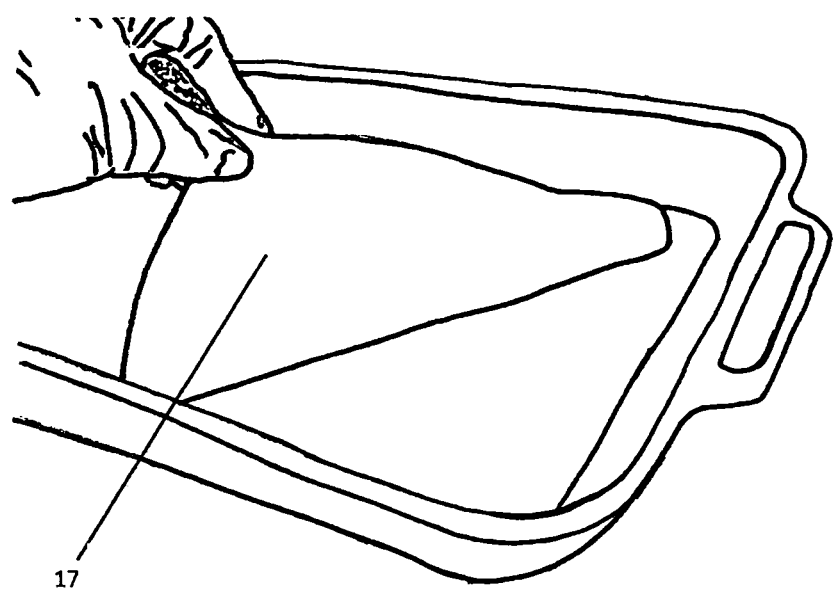
FIG. 3 illustrates a view of a microbial cellulose film being harvested from a dish in accordance with the invention.

Grow Microbial Cellulose in Vitro and Apply to Biomaterial Surfaces a. Inoculate 200 ml of a common liquid medium used to culture bacteria, such as a buffered S&H medium, with one colony of microbial cellulose producing bacteria *Acetobacter xylinus*.
b. Incubate culture at 30° C. for 24-96 hours to form a biofilm thereon.
c. Harvest the cellulose biofilm 17 (FIG. 3)
d. Apply the cellulose to the surface of partially or fully myceliated AS thereby forming a bio-film like skin.
e. Allow the biomaterial to grow into the cellulose if further biofilm integration is required for material performance.
f. Terminate growth of material

EXAMPLE 3

Grow Microbial Biofilm In Vitro and Apply within Biomaterials a. Inoculate 200 ml of LB media with colony of biofilm producing bacteria *Bacillus subtilis* sp. bacteria
b. Incubate culture at 37° C. until the biofilm has reached optimal qualities and quantities (24-96 hours)
c. Harvest the biofilm by either direct biofilm extraction (FIG. 3), or for other biofilms that remain homogenous in the media, the entirety of the culture will be harvested.
d. Mix the harvested biofilm into myceliated or non-myceliated AS.
e. Hot press the material to fully bond all components.
f. Terminate the growth of material.

EXAMPLE 4

Bacterial Antimicrobials Produced In Situ a. Inoculate 100 ml LB media with one colony of *Streptomycin natalensis*. Grow culture at 37° C. to mid log phase.
b. Co-inoculate 600 g AS with both bacteria (*S. natalensis*) and fungi (*Ganoderma*) species using 100 ml mid log bacteria culture, and <20% fungal inoculum.
c. Incubate co-inoculated material at room temperature for 6 days.
d. Heat inactive microbial growth by desiccation.
e. Material will have enhanced resistance to bio burden throughout the incubation process resulting in limited loss of product due to contaminated material.

EXAMPLE 5

Bacterial Antimicrobials Produced In Vitro a. Inoculate 100 ml LB media with one colony of *Streptomycin alboniger*. Grow culture at 37° C. to mid log phase.
b. Filter the bacteria out of the culture using 0.2 um filters thus reducing the culture to spent media spiked with antimicrobial compounds (may also retain the bacteria if co-habitation of the antimicrobial producing bacteria and fungus is needed in next steps).
c. Add 100 ml of the antimicrobial supernatant to 600 g AS, and incubate the treated AS for 3 hours at room temperature.
d. Inoculate the treated AS with <20% Fungi (*Ganoderma*), and incubate for 6 days at room temperature.
e. Terminate all microbial growth by desiccation.

In all of the processes described above, the inoculated agricultural substrates may be placed in molds of predetermined shape in order to produce products having a shape corresponding to the shape of the interior of the mold.

The invention thus provides a process of making a bacterial biofilm that can be used as a bio-resin and as a surface application for myceliated and non-myceliated biomaterials.

What is claimed is:

1. A process of producing a bacterial antimicrobial in situ comprising the steps of:
    inoculating 100 ml of a lysogeny broth media with one colony of *Streptomyces natalensis* to form a culture;
    growing the culture at 37° C. to mid log phase;
    co-inoculating 600 g of agricultural substrate with 100 ml of said mid log culture and <20% v/v fungal inoculum;
    incubating the co-inoculated substrate at room temperature for 6 days; and
    heating the incubated co-inoculated substrate to terminate microbial growth by desiccation.

2. The process as set forth in claim 1, wherein said fungal inoculum is made from *Ganoderma*.

3. A process of producing a bacterial antimicrobial comprising the steps of:
    inoculating a lysogeny broth media with one colony of bacteria to form a culture;
    growing the culture to mid log phase;
    co-inoculating an agricultural substrate with said mid log bacterial culture and a fungal inoculum;
    incubating the co-inoculated substrate at room temperature; and thereafter heating the incubated co-inoculated substrate to terminate microbial growth by desiccation.

4. The process as set forth in claim 3, wherein said bacteria is one of *Streptomyces natalensis* and *Streptomyces alboniger*.

5. The process as set forth in claim 3, wherein said step of co-inoculating the agricultural substrate includes:
    adding said mid log bacterial culture to the substrate;
    incubating the substrate to allow said bacteria to excrete a biofilm into said substrate;
    inoculating the substrate with the fungal inoculum; and
    incubating the substrate to allow said fungal inoculum to grow a network of interconnected mycelia cells extending through and around discrete particles of the substrate.

* * * * *